United States Patent [19]

Gschwend

[11] 4,356,176
[45] Oct. 26, 1982

[54] DIBENZ[c,e]AZEPINES
[75] Inventor: Heinz W. Gschwend, New Providence, N.J.
[73] Assignee: Ciba-Geigy Corporation, Ardsley, N.Y.
[21] Appl. No.: 206,938
[22] Filed: Nov. 14, 1980

Related U.S. Application Data

[62] Division of Ser. No. 106,645, Dec. 26, 1979, Pat. No. 4,315,926.

[51] Int. Cl.³ .................. A61K 31/435; C07D 401/04
[52] U.S. Cl. .................................. 424/244; 260/244.4
[58] Field of Search ..................... 260/244.4; 424/244

[56] References Cited
U.S. PATENT DOCUMENTS
4,022,801 5/1977 Schwend .................... 260/244.4 X OTHER PUBLICATIONS
Z. Naturforsch 324, 425 (1974).

Primary Examiner—David B. Springer
Attorney, Agent, or Firm—Norbert Gruenfeld

[57] ABSTRACT

7-Aryl-5H-dibenz[c,e]azepines, e.g., those of the formula

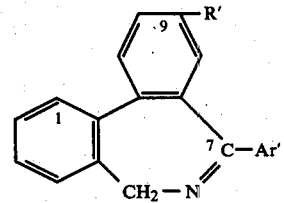

Ar' = phenyl, furyl, thienyl, pyridyl or phenyl subst. by alkyl, OH, alkoxy, halo or $CF_3$;

R' = halo or $CF_3$

N-oxides or salts thereof are anxiolytic, tranquilizing and anticonvulsant agents.

5 Claims, No Drawings

DIBENZ[c,e]AZEPINES

CROSS REFERENCE TO RELATED APPLICATION

This is a divisional of application Ser. No. 106,645, filed Dec. 26, 1979, and now U.S. Pat. No. 4,315,926.

SUMMARY OF THE INVENTION

The present invention concerns and has for its object the provision of new 7-aryl-5H-dibenz[c,e]azepines, preferably those of Formula I

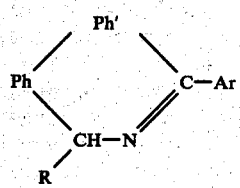

wherein each of Ph and Ph' is 1,2-phenylene, unsubstituted or substituted by one or more than one member selected from the group consisting of lower alkyl, hydroxy, lower alkoxy, halogeno and trifluoromethyl; Ar is monocyclic isocyclic or mono-(oxa, thia or aza)-cyclic aryl, unsubstituted or substituted as Ph or Ph', and R is hydrogen, lower alkyl, hydroxy, lower alkoxy, amino, mono- or di-lower alkylamino; lower alkanoyl derivatives; the 6-N-oxide and pharmaceutically acceptable acid addition salts thereof, as well as of corresponding pharmaceutical compositions and of methods for the preparation and application of these products, which are useful anxiolytics, tranquilizers and anticonvulsants.

DESCRIPTION OF THE PREFERRED EMBODIMENTS

The 1,2-phenylene radicals Ph and Ph', as well as the aryl radicals Ar, are unsubstituted or substituted by one or more than one, preferably by one or two, of the same or different substituents selected from the group consisting of lower alkyl, e.g. methyl, ethyl, n- or i-propyl or -butyl; hydroxy; lower alkoxy, e.g. methoxy, ethoxy, n- or i-propoxy or -butoxy; halogeno, e.g. fluoro, chloro or bromo; or trifluoromethyl. The term "lower," referred to above and hereinafter in connection with organic radicals or compounds respectively, defines such with up to 7, preferably up to 4, and especially 1 or 2 carbon atoms.

Preferred 1,2-phenylene radicals Ph and Ph' are 1,2-phenylene, (lower alkyl)-1,2-phenylene, (hydroxy)-1,2-phenylene, (lower alkoxy)-1,2-phenylene, (halogeno)-1,2-phenylene or (trifluoromethyl)-1,2-phenylene; and preferred aryl radicals Ar are phenyl, (lower alkyl)-phenyl, (hydroxy)-phenyl, (lower alkoxy)-phenyl, (halogeno)-phenyl, (trifluoromethyl)-phenyl; furyl, (lower alkyl)-furyl, thienyl, (lower allyl)-thienyl, pyridyl or (lower alkyl)-pyridyl.

R in 5-position is preferably a hydrogen atom, but also said lower alkyl, hydroxy, alkoxy, amino, mono- or di-alylyamino groups; above all methyl, hydroxy, methoxy or amino.

The lower alkanoyl derivatives are derived from the phenols (Ph=hydroxyphenylene) and/or the 5-(hydroxy or amino)compounds, and preferably acetic, propionic or pivalic acid. Said acid addition salts are derived from the pharmaceutically acceptable acids listed below.

The compounds of the invention exhibit valuable pharmacological properties, for example, tranquilizing, anticonvulsant and especially antianxiety effects. This can be demonstrated in animal tests, using advantageously mammals, such as mice, rats or monkeys, as test objects. The compounds of the invention can be applied to said mammals enterally, e.g., orally, or parenterally, such as subcutaneously, intraperitoneally or intravenously, e.g., in the form of starchy suspensions or aqueous solutions respectively. The dosage may range between about 0.1 and 1,000 mg/kg/day, preferably between about 1 and 100 mg/kg/day, advantageously between about 3 and 30 mg/kg/day.

Antianxiety effects are observed, for example, according to the Cook-Davidson conflict procedure, using male Wistar rats which are maintained at 80% of normal body weight by dietary-, but not water-restriction. They are trained to press a lever within a conditioning chamber, also containing a liquid dipper, a house light, a speaker and a grid-floor. Both lever and grid are connected to an electric shock source and the chamber is situated in a sound-attenuated room in which a white noise-source is activated during testing, in order to mask any extraneous auditory cues. Each session of 47 minutes duration consists of two alternating schedules. The first is a Variable Interval (VI) schedule of 30 seconds, lasting for 5 minutes, during which a sweetened, condensed milk reinforcement is delivered following the first lever-press after the 30 seconds have elapsed, and a drug-induced decrement of this performance is taken as an indication or a neurological deficit. Immediately following the VI-schedule both a 1000 Hz tone and a light-cue are activated, indicating the commencement of the second, Fixed Ratio (FR) schedule, lasting for 2 minutes, wherein the milk reinforcement is delivered concomitant with an electric foot shock immediately following the tenth response, thereby establishing a conflict situation. The intensity of said shock ranges between 2.0 and 3.6 mA, varying with each animal, in order to adjust them to about 25–100 responses during this schedule over the entire session. A drug-induced enhancement or performance during the FR-schedule is taken as indication of antianxiety effects, as exhibited by said compounds of this invention.

These compounds also have characteristic effects on the electroencephalogram (EEG) of male squirrel monkeys. They received, under anesthesia, 6 stainless steel screw epidural electrodes inserted into the skull, overlying the right and left occiptal and parietal cortices, as well as the left frontal cortex and vertex. Wires are attached to the multipin-connector, which is affixed to the skull with dental cement. Spontaneous EEG-data are collected while the monkey is restrained in a small electrically shielded chamber, and the multichannel EEG is continuously recorded onto magnetic tape, while sample-recordings are made on paper. The magnetic record is converted into digital form and processed by computer, using a baseline zero-crossing analysis. The EEG from a single differential lead (right occipital to vertex) is analyzed, whereby frequency and amplitude of both the primary and secondary wave are quantified and the frequency distribution is computed for the percentage of total EEG-activity from 0 to 64 Hz.

After at least 2 weeks recovery after surgery the monkeys receive placebo for accommodation recording sessions, lasting 30 minutes before and 3 hours after treatment, and 4 or 5 placebo recordings are usually sufficient. One week separates treatment with various doses of the same drug, and two weeks separate treatment with different drugs, e.g. diazepam for comparison purposes. According to the results obtained, the EEG-profiles caused by the compounds of the invention resemble those produced by diazepam, i.e. high frequency activity is increased, mid-range frequency is diminished and the activity below 8 Hz remains essentially unchanged.

Thus, for example, administration of the 9-chloro-7-(o-fluorophenyl)-5H-dibenz[c,e]azepine, or a salt thereof, e.g. its mesylate, which are characteristic compounds of the invention, when applied to rats at oral doses of 10, 30 and 100 mg/kg/day, increase their FR-responses with increasing doses, but do not suppress the VI-responding in said Cook-Davidson test. Moreover, oral doses of 10 and 30 mg/kg/day increase in the EEG of squirrel monkeys the higher frequencies of the primary and secondary wave, but reduce this activity between 8 and 16 Hz, which changes become evident as early as 30 minutes after treatment and persist throughout the entire recording session, but no alterations are apparent below 8 Hz.

Moreover, the compounds of the invention antagonize metrazole in rats, as well as picrotoxin- or threshold-seizures induced by minimal electro-shock in mice. Therefore, they are useful in combatting anxiety problems similar to those treated with diazepam, and in the prevention of petit mal seizures. In contrast to diazepam, said characteristic compounds of the invention appear to be devoid of neurological deficit liability at doses where antianxiety effects are already established. Finally, the compounds of the invention are also valuable intermediates in the preparation of other useful products, especially of corresponding pharmaceutical compositions.

Particularly useful are compounds of Formula I, wherein each of Ph and Ph' is 1,2-phenylene, unsubstituted or substituted by one or two of the same or different members selected from the group consisting of lower alkyl, hydroxy, lower alkoxy, halogeno and trifluoromethyl; Ar is phenyl, furyl, thienyl or pyridyl, unsubstituted or substituted as Ph or Ph', and R is hydrogen, lower alkyl, hydroxy, lower alkoxy, amino, mono- or di-lower alkylamino; lower alkanoyl derivatives, the 6-N-oxide or pharmaceutically acceptable acid addition salts thereof.

Preferred compounds of Formula I are those wherein each of Ph and Ph' is 1,2-phenylene, (lower alkyl)-1,2-phenylene, (hydroxy)-1,2-phenylene, (lower alkoxy)-1,2-phenylene, (halogeno)-1,2-phenylene or (trifluoromethyl)-1,2-phenylene; Ar is phenyl, (lower alkyl)-phenyl, (hydroxy)-phenyl, (lower alkoxy)-phenyl, (halogeno)-phenyl, (trifluoromethyl)-phenyl, furyl, (lower alkyl-furyl, thienyl, (lower alkyl)-thienyl, pyridyl or (lower alkyl)-pyridyl, and R is hydrogen or lower alkyl; or pharmaceutically acceptable acid addition salts thereof.

Outstanding on account of their anxiolytic, tranquilizing and anticonvulsant effects are the compounds of Formula II

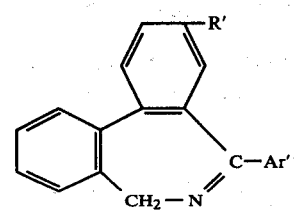

wherein Ar' is phenyl, 2-furyl, 2-thienyl, 2-pyridyl or phenyl ortho-substituted by hydroxy, alkyl or alkoxy with up to 4 carbon atoms each, fluoro, chloro, bromo or trifluoromethyl, and R' is fluoro, chloro, bromo or trifluoromethyl; or pharmaceutically acceptable acid addition salts thereof.

Most preferred are those compounds of Formula II, wherein Ar' is ortho-(fluoro or chloro)-phenyl and R' is bromo, fluoro or chloro, or pharmaceutically acceptable acid addition salts thereof.

The compounds of the invention are prepared according to conventional methods, for example, by ring-closing compounds of Formula III

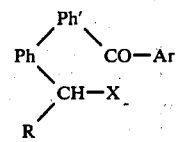

wherein X is amino and, if desired, converting any resulting product into another compound of the invention.

Said ring-closing intramolecular condensation is preferably performed under neutral or mildly basic conditions, for example, in anhydrous organic solvents, such as lower alkanols, e.g., methanol or ethanol; open or cyclic aliphatic ethers, e.g., diethyl ether or tetrahydrofuran and/or halogenated hydrocarbons, e.g., methylene chloride, and in the presence or absence of ammonia or other nitrogen bases, e.g., pyridine or a tri-lower alkylamine at moderate temperatures, e.g., between 0° and 100°.

The starting material can be prepared by reacting either compounds of Formula III, wherein X is hydrogen, with N-bromosuccinimide; or those wherein X is di-lower alkylamino or lower alkyleneimino, e.g., dimethylamino or pyrrolidino, with cyanogen bromide, and condensing the resulting compounds wherein X is bromine with ammonia. Any new precursor of Formula III, wherein X is different from amino, can be prepared analogous to the methods illustrated by Examples 1-8 herein.

Those compounds of Formula I with R being hydrogen or lower alkyl can also be prepared by adding to the compounds of Formulae IV or V

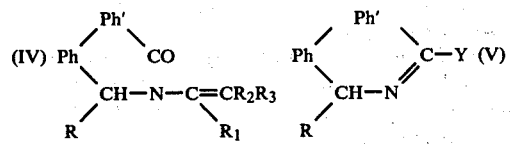

the metal compound $Ar^{\ominus}M^{\oplus}$, wherein each of $R_1$, $R_2$ and $R_3$ is hydrogen, lower alkyl or phenyl; Y is halogen, $Ph-SO_3$, lower alkoxy or alkylthio and M is an alkali metal or halomagnesium, and hydrolyzing the metal-adduct derived from IV under neutral or basic conditions and, if desired, converting any resulting product into another compound of the invention.

The addition of said aryl alkali metal or Grignard compounds is preferably performed in said open or cyclic ethers at low temperatures, e.g. between about −70° and room temperature, and said hydrolysis may simply be performed with cold water or aqueous ammonium salt solutions.

The dibenzoazepinones of Formula IV and V are either known or, if new, can be prepared according to known procedures or by the methods illustrated by Example 5 herein, which are similar to said process for the compounds of Formula III, i.e. the generation of an $\alpha$-bromoalkyl group from an unsubstituted R—CH$_2$ or tert. amino—CH—R moiety and, if necessary, followed by introduction of the olefinic bond in the N-substituent of IV by dehydrohalogenation. Compounds V are advantageously obtained from the corresponding lactams and strong esterifying or alkylating agents, such as phosphorus halides or oxyhalides, arylsulfonyl halides or trialkyloxonium salts, e.g., tetrafluoroborates.

The resulting compounds of the invention can be converted into each other according to conventional methods. For example, resulting compounds with hydroxy within Ph, Ph' and/or Ar, or alkali metal salts thereof, can be reacted with reactive esters of lower alkanols, preferably esters with strong acids, such as hydrohalic, aliphatic or aromatic sulfonic acids, e.g. lower alkyl chlorides, bromides, iodides; lower alkyl alkane- or benzenesulfonates, e.g. the mesylate or tosylate, to yield the corresponding lower alkoxy compounds. Moreover, compounds of Formula I can be converted into their N-oxides, for example, by treating them with mild oxidation agents, such as hydrogen peroxide, aliphatic or aromatic percarboxylic acids, e.g. peracetic or perbenzoic acid.

Finally, a resulting base can be converted into a corresponding acid addition salt, preferably with the use of an acid or anion exchange preparation, or resulting salts can be converted into the corresponding free bases, for example, with the use of a base, such as a metal hydroxide, basic salt, ammonia, amine or cation exchange preparation, e.g. an alkali metal hydroxide or carbonate. Said acid addition salts are preferably those of pharmaceutically acceptable inorganic or organic acids, such as strong metalloidic acids, for example, hydrohalic, e.g. hydrochloric or hydrobromic acid; sulfuric, phosphoric, nitric or perchloric acid; aliphatic or aromatic carboxylic or sulfonic acids, e.g. formic, acetic, propionic, succinic, glycollic, lactic, malic tartaric, citric, ascorbic, maleic, hydroxymaleic, pyruvic, phenylacetic, benzoic, 4-aminobenzoic, anthranilic, 4-hydroxybenzoic, salicylic, 4-aminosalicylic, embonic, nicotinic; methanesulfonic, ethanesulfonic, hydroxyethanesulfonic, ethylenesulfonic, halogenobenzenesulfonic, toluenesulfonic, naphthalenesulfonic, sulfanilic or cyclohexylsulfamic acid. These or other salts, for example, the pidrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

Resulting mixtures of isomers can be separated into the single isomers by methods in themselves known, e.g. by fractional distillation, crystallization and/or chromatography.

The invention further includes any variant of the above processes in which an intermediate product, obtainable at any stage thereof is used as starting material, and any remaining steps are carried out, or said process is discontinued at any stage thereof, or in which the starting materials are formed under the reaction conditions, e.g. those of Formula III with X=NH$_2$, or in which the reaction components are used in the form of their salts. Mainly those starting materials should be used in the reactions of the invention that lead to the formation of those compounds indicated above as being especially valuable, e.g. those of Formula II.

The pharmacologically active compounds of the invention are useful in the manufacture of pharmaceutical compositions containing an effective amount thereof in conjunction or admixture with excipients suitable for either enteral or parenteral application. Preferred are tablets and gelatin capsules comprising the active ingredient together with (a) diluents, e.g. lactose, dextrose, sucrose, mannitol, sorbitol, cellulose and/or glycine, (b) lubricants, e.g. silica, talcum, stearic acid, its magnesium or calcium salt and/or polyethyleneglycol, for tablets also (c) binders, e.g. magnesium aluminum silicate, starch paste, gelatin, tragacanth, methylcellulose, sodium carboxymethylcellulose and/or polyvinylpyrrolidone, if desired, (d) disintegrants, e.g. starches, agar, alginic acid or its sodium salt, enzymes of the binders or effervescent mixtures and/or (e) absorbents, collorants, flavors and sweeteners. Injectable compositions are preferably aqueous isotonic solutions or suspensions, and suppositories are advantageously made from fatty emulsions or suspensions. They may be sterilized and/or contain adjuvants, such as preserving, stabilizing, wetting or emulsifying agents, solution promoters, salts for regulating the osmotic pressure and/or buffers. They may also contain other therapeutically valuable substances. Said pharmaceutical compositions are prepared according to conventional mixing, granulating or coating methods respectively and contain about 0.1 to 75%, preferably about 1 to 50% of the active ingredient.

The following examples, illustrating the invention, are not to be construed as being limitations thereon. Temperatures are given in degrees centigrade, all parts wherever given are parts by weight and, if not otherwise stated, all evaporations are carried out under reduced pressure, e.g. between about 0.1 and 15 mmHg.

EXAMPLE 1

The solution of 587 g of 2-(o-bromomethylphenyl)-5-chloro-2'-fluorobenzophenone in 400 ml of tetrahydrofuran is added during 15 minutes to the solution of 500 g of anhydrous ammonia in 6,000 ml of anhydrous ethanol while stirring at 1°-5°. After stirring overnight at room temperature the mixture is evaporated, the residue taken up in 2,000 ml of methylene chloride and 2,000 ml of ice water and the pH of the aqueous layer adjusted to 8 with saturated aqueous sodium carbonate. It is separated, extracted with another 1,000 ml of methylene chloride, the combined organic solutions dried, filtered and evaporated. 362 g of the residual oil are dissolved in 600 ml of anhydrous ethanol and the solution combined with 107.5 g of methane sulfonic acid while stirring. The mixture is kept overnight at room temperature and allowed to stand at −18° for another day. The precipitate formed is collected, washed with cold ethanol and dried at room temperature, to yield the 9-chloro-7-(o-fluorophenyl)-5H-dibenz[c,e]azepine mesylate of Formula II with Ar′=2—F—$C_6H_4$ and R′=Cl, melting at 186°–187°.

The starting material is prepared as follows: To the solution of 1,082 g of isopropylamine in 2,000 ml of methylene chloride and 3,250 ml of water, that of 1,300 g of o-fluorobenzoyl chloride in 2,600 ml of methylene chloride is added during 2 hours while stirring at 2°–9°. Stirring is continued at room temperature overnight, the organic layer is separated and the aqueous phase extracted with 1,000 ml of methylene chloride. The combined organic solutions are dried, evaporated and the residue recrystallized from 1,000 ml of hexane, to yield the N-isopropyl-o-fluorobenzimide melting at 76°–79°.

The mixture of 375 g thereof and 290 ml of thionyl chloride is refluxed for 15 minutes, evaporated, the residue distilled and the fraction boiling at 66°/1.5 mmHg collected, to yield the N-isopropyl-o-fluorobenzimide chloride.

To the solution of 499 g thereof in 3,000 ml of anhydrous diethyl ether, that of 2-lithio-4-chloroanisole prepared by stirring the mixture of 392 g of p-chloroanisole, 2,750 ml of diethyl ether and 1,250 ml of 2.4 molar n-butyl-lithium for 25 hours at 2°–3°, is added during 90 minutes while stirring under nitrogen at −5° to −12°. The mixture is allowed to warm to room temperature while stirring for 20 hours. It is again cooled to 0° and 240 ml of 50% aqueous sodium hydroxide are added, followed by 1 mg of ice and 1,000 ml of water. After stirring for 30 minutes the organic layer is separated and the aqueous phase extracted with diethyl ether. The combined organic solutions are dried, filtered, evaporated and the residue is taken up in 1,000 ml of hexane. The solution is decolorized with charcoal, filtered, the filtrate chilled to −18° for 20 hours and the precipitate collected, to yield the N-[α-(o-fluorophenyl)-5-chloro-2-methoxybenzylidene]-isopropylimine melting at 72°–74°.

The solution of 472 g thereof in 2,000 ml of tetrahydrofuran is added during 40 minutes to the Grignard solution prepared from 48 g of magnesium, 5 crystals of iodine, 430 g of o-bromobenzyl-dimethylamine and 3,000 ml of tetrahydrofuan, while stirring under nitrogen at 5°–10°. The mixture is refluxed for 30 hours, cooled to room temperature and combined with 400 g of ice and 1,000 ml of 5 N-hydrochloric acid. It is concentrated to about half its volume, the concentrate diluted with 3,000 ml of methylene chloride and adjusted with about 1,500 ml of concentrated aqueous ammonia to the pH=10, while adding ice also. The mixture is stirred for one hour, the organic layer is separated and the aqueous phase extracted with 1,000 ml of methylene chloride. The combined organic solutions are dried, filtered, evaporated and the residue heated to 120°/1 mmHg for 2 hours in order to remove unreacted material. The residue is dissolved in 1,100 ml of acetone, the solution combined with that of 178 g of maleic acid in 1,000 ml of acetone and the precipitate collected after standing overnight at room temperature, to yield the 5-chloro-2-(o-dimethylaminomethylphenyl)-2′-fluorobenzophenone maleate melting at 164°–165°.

The mixture of 542 g thereof, 2,000 ml of methylene chloride, 300 ml of 50% aqueous sodium hydroxide and 2,000 ml of ice water is well shaken, the organic layer separated and the aqueous phase extracted twice more with 1,000 and 500 ml of methylene chloride. The combined organic solutions are dried, filtered, diluted with 1,500 ml of methylene chloride and 130 g of cyanogen bromide in 1,000 ml of methylene chloride are added during 40 minutes while stirring at 1°. Stirring is continued for 2 hours at 1° and the mixture is evaporated at 35°–40°, to yield the 2-(o-bromomethylphenyl)-5-chloro-2′-fluorobenzophenone.

EXAMPLE 2

The solution of 5.4 g of 2-(o-bromomethylphenyl)-5-bromo-2′-fluorobenzophenone in 10 ml of ethanol is added slowly to the solution of 150 ml of saturated ethanolic ammonia while stirring at room temperature. After 2 days the mixture is evaporated, the residue taken up in methylene chloride and the solution washed with aqueous sodium carbonate. The organic layer is dried, evaporated and 5 g of the residue chromatographed on 50 g of silica gel, using first toluene, then toluene-diethyl ether (9:1) as the eluent. The later fraction is evaporated and the residue crystallized from hexane to yield the 9-bromo-7-(o-fluorophenyl)-5H-dibenz[c,e]azepine melting at 104°–105°.

The starting material is prepared as follows: The solution of 110 g of 5-bromosalicylic acid in 900 ml of water and 48 g of sodium hydroxide is stirred while 60 ml of dimethyl sulfate are added. The mixture is stirred at 70° for 3 hours, whereupon 50 ml of 50% aqueous sodium hydroxide are added, followed slowly by 60 ml of dimethyl sulfate. After stirring at 70° for 6 hours the last step is repeated and the mixture warmed 17 hours longer. It is cooled in an ice bath, filtered, the filtrate stirred with methylene chloride and neutralized with cold 5 N aqueous hydrochloric acid. The organic phase is separated, dried and evaporated to yield the 5-bromo-2-methoxybenzoic acid melting at 115°–117°.

The solution of 62.5 g thereof in 120 ml of thionyl chloride is refluxed for 2 hours and the residue dissolved in 300 ml of methylene chloride. The solution is added to that of 45 g of 2-amino-2-methylpropanol in 300 ml of methylene chloride while cooling with ice. The mixture is stirred at room temperature for 3 hours, then washed with aqueous sodium carbonate, dried and evaporated to yield N-(2-hydroxy-1-methyl-2-propyl)-5-bromo-2-methoxybenzamide.

58 g thereof are stirred for 1 hour with 55 ml of thionyl chloride, the mixture is diluted with 300 ml of diethyl ether and the supernatant solution discarded. The oily residue is shaken with methylene chloride and ice cold aqueous sodium hydroxide, the organic layer is dried and evaporated to give the 2-(5-bromo-2-methoxyphenyl)-4,4-dimethyl-2-oxazoline melting at 41°.

To the ice cold solution of 17.8 g thereof in 180 ml of tetrahydrofuran is added dropwise the Grignard solution prepared from 4.5 g of magnesium and 32 g of o-bromotoluene in 200 ml of diethyl ether. After addition the mixture is stirred for 2 hours at room temperature, cooled again in an ice bath and combined with saturated aqueous ammonium chloride. The organic layer is separated, washed with saturated aqueous sodium chloride, dried and evaporated to give the 2-(5-bromo-2-o-tolylphenyl)-4,4-dimethyl-2-oxazoline.

The mixture of 22.4 g thereof, 130 ml of acetone and 60 ml of methyl iodide is refluxed for 16 hours while stirring. Thereafter it is cooled with ice and the precipitate filtered off to yield the corresponding N-methiodide salt melting at 184°–186°.

The solution of 22 g thereof in 660 ml of anhydrous ethanol is stirred in an ice bath and 1.8 g of sodium borohydride are added in portions. After 1 hour it is made acidic with 2 N aqueous hydrochloric acid and stirred for another hour at room temperature. It is evaporated, the residue stirred in diethyl ether and cold water, the organic phase separated, dried, evaporated and the residue crystallized from diethyl ether to give the 5-bromo-2-o-tolylbenzaldehyde melting at 71°–73°.

The solution of 4.0 g thereof in 35 ml of dry diethyl ether is added slowly to that prepared from 10 ml of 1.6 molar n-butyl lithium in hexane and 35 ml of diethyl ether (kept under nitrogen) and 2.8 g of o-bromo-fluorobenzene in 35 ml of diethyl ether at −70°. The mixture is then stirred for 1 hour without external cooling, washed with water, the organic phase separated, dried and evaporated, to yield the α-(5-bromo-2-o-tolylphenyl)-o-fluorobenzyl alcohol.

To the solution of 5.6 g thereof in 300 ml of diethyl ether, 14.5 ml of 2 molar aqueous chromic acid solution is added slowly while stirring at 0°. After 3 hours the mixture is washed with 10% aqueous sodium thiosulfate, 2% aqueous sodium hydroxide and water, the organic phase separated, dried and evaporated. The residue is chromatographed on silica gel, using hexanediethyl ether (9:1) as eluent, to yield the 5-bromo-2′-fluoro-2-(o-tolyl)-benzophenone.

The mixture 4.46 g thereof, 130 ml of carbon tetrachloride, 2.36 g of N-bromosuccinimide and 0.2 g of dibenzoyl peroxide is refluxed with stirring for 105 minutes. After cooling in an ice bath it is filtered and the solvent evaporated to yield the 2-(o-bromomethylphenyl)-5-bromo-2′-fluorobenzophenone.

Analogously the 9-chloro-7-(o-fluorophenyl)-3-(methoxy or chloro)-5H-dibenz[c,e]azepines melting at 142°–143° and 155°–156° respectively, as well as the 9- or 10-chloro-7-(o-fluorophenyl)-5H-dibenz[c,e]azepines melting at 105°–106° and 137°–138° respectively, are prepared.

EXAMPLE 3

The solution of 2.8 g of 2-(o-bromomethylphenyl)-5-chlorobenzophenone in 20 ml of tetrahydrofuran is added dropwise to the solution of 130 ml of saturated ethanolic ammonia while stirring. After 2 days' standing at room temperature the mixture is evaporated, the residue taken up in methylene chloride, the solution washed with aqueous sodium carbonate, dried, evaporated and the residue crystallized from methanol to give the 9-chloro-7-phenyl-5H-dibenz[c,e]azepine melting at 118°–119°.

The starting material is prepared as follows: The mixture of 17 g of 2-(5-chloro-2-o-tolylphenyl)-4,4-dimethyl-2-oxazoline (prepared as shown in Example 2), 150 ml of p-dioxane, and 160 ml of 5 N aqueous hydrochloric acid is refluxed for 3 days while stirring. It is evaporated, the residue taken up in diethyl ether, the organic phase separated, dried, evaporated and the residue crystallized from hexane to yield the 3-chloro-6-o-tolylbenzoic acid melting at 135°–137°.

The mixture of 6.3 g thereof and 15 ml of thionyl chloride is refluxed for 30 minutes and evaporated. The residue is dissolved in 50 ml of methylene chloride, the solution added dropwise to the cold solution of 39 ml of 2 N aqueous sodium hydroxide, 10.7 ml of tert butylamine and 70 ml of methylene chloride. After stirring the mixture for 3 hours at room temperature, the organic layer is separated, dried and evaporated. The residue is dissolved in 75 ml of thionyl chloride, the solution refluxed for 2 hours, evaporated, the residue distilled and the fraction boiling at 130°/0.9 mm Hg collected, to yield the 3-chloro-6-(o-tolyl)-benzonitrile melting at 62°–65°.

The solution of 4.0 g thereof in 160 ml of diethyl ether is cooled in an ice bath whereupon 40 ml of 0.5 molar ethereal phenyl lithium are added. The mixture is stirred for 16 hours at room temperature, diluted with water, the organic layer separated, dried and evaporated. The residue is dissolved in 50 ml of ethanol and 30 ml of 2 N hydrochloric acid, the mixture refluxed for 2 hours and evaporated. The residue is taken up in water, the mixture extracted with diethyl ether, the extract treated with activated charcoal, evaporated and the residue chromatographed on silica gel using hexanediethyl ether (9:1) as eluent. Fractions 2 and 3 are collected and evaporated to yield the 2-(o-tolyl)-5-chlorobenzophenone. This is brominated with N-bromosuccinimide as described in Example 2, to yield the 2-(o-bromomethylphenyl)-5-chlorobenzophenone.

In an aqueous manner the 9-chloro-7-(2-thienyl)-5H-dizenz[c,e]azepine is prepared, melting at 108°–110°.

EXAMPLE 4

The solution of 4.5 g of 5-chloro-2-(o-dimethylaminomethyl-phenyl)-2-benzoylpyridine in 120 ml of methylene chloride is treated during 4 hours with 13.7 ml of 0.94 molar cyanogen bromide in methylene chloride. The mixture is evaporated, the residue dissolved in 200 ml of saturated methanolic ammonia, and the solution evaporated after 2 days. The residue is taken up in aqueous sodium carbonate, the mixture extracted with diethyl ether, the extract washed with saturated aqueous sodium chloride, decolorized with activated charcoal, evaporated and the residue crystallized from diethyl ether to give the 9-chloro-7-(2-pyridyl)-5H-dibenz[c,e]azepine melting at 153°–155°.

The starting material is prepared as follows: 3.8 g of 3-chloro-6-o-tolyl-benzonitrile (described in Example 3) is brominated as described in Example 2, and the residue dissolved in 25 ml of methylene chloride. The solution is added slowly to that of 14 g of liquid dimethylamine in 100 ml of methylene chloride while stirring at 0°. The mixture is stirred at room temperature for 16 hours, evaporated and the residue stirred with diethyl ether and 1 N hydrochloric acid. The aqueous phase is separated, combined with methylene chloride and basified with cold 2 N aqueous sodium hydroxide. The organic layer is separated, dried and evaporated to yield the 3-chloro-6-(o-dimethylaminomethyl-phenyl)-benzonitrile.

The solution of 3.5 g thereof in 65 ml of diethyl ether is slowly added at −10° to the solution of 2-lithiopyridine, prepared from 2.45 g of 2-bromopyridine and 9.7 ml of 1.6 molar n-butyl lithium in hexane and 40 ml of diethyl ether. The mixture is allowed to warm to 25° and stirred for 16 hours. It is washed with saturated aqueous sodium chloride, dried and evaporated. The residue is dissolved in 250 ml of 2 N hydrochloric acid and the solution refluxed for 20 hours. It is cooled to 5°, made basic with sodium hydroxide and extracted with diethyl ether. The extract is treated with activated charcoal, filtered and evaporated to give the 3-chloro-6(o-dimethylaminomethylphenyl)-2-benzoylpyridine.

EXAMPLE 5

The solution of 19 g of o-bromo-fluorobenzene in 220 ml of diethyl ether is added very slowly to the solution of 43 ml of 2.56 molar n-butyl lithium in hexane and 22 ml of diethyl ether while stirring under nitrogen at −70°. The mixture is stirred 10 minutes longer whereupon the solution of 20 g of 3-chloro-6,7-dihydro-6-vinyl-dibenz[c,e]azepin-5-one in 200 ml of tetrahydrofuran is added at −70°. The mixture is stirred at room temperature for 16 hours, washed with cold water, the organic phase separated, dried and evaporated. The residue is dissolved in toluene, the solution chromatographed on 100 g silica gel, the toluene-eluate evaporated, the residue dissolved in acetone and the solution neutralized with methane sulfonic acid, to yield the 9-chloro-7-(o-fluorophenyl)-5H-dibenz[c,e]azepine mesylate melting at 184°–186°, it is identical wit that obtained according to Example 1.

The starting material is prepared as follows: The mixture of 75 g of 5-chloro-2-methoxybenzoic acid and 50 ml of thionyl chloride is stirred at room temperature for one hour and evaporated. The residue is dissolved in 400 ml of methylene chloride and the solution added slowly to the cold stirred mixture of 27 g of 2-aminoethanol, 170 ml of methylene chloride and 320 ml of saturated aqueous sodium carbonate. After 4 hours, the organic layer is separated, dried and evaporated to yield the N-2-hydroxyethyl-5-chloro-2-methoxybenzamide.

The mixture of 93 g thereof and 100 ml of thionyl chloride is stirred at room temperature for 80 minutes, evaporated and the residue stirred with the mixture of 400 ml of methylene chloride, 120 ml of 50% aqueous sodium hydroxide and 1 g of tetrabutylammonium hydrogensulfate for 2 hours at room temperature. The organic layer is separated, dried, evaporated and the residue crystallized from diethyl ether, to yield the 2-(5-chloro-2-methoxyphenyl)-oxazoline melting at 100°–101°.

To the solution of 53 g thereof in 300 ml of tetrahydrofuran the Grignard-solution prepared from 80 g of N,N-dimethyl-o-bromobenzylamine, 9.5 g of magnesium and 600 ml of diethyl ether is added slowly while stirring at 0°. The mixture is stirred at room temperature for 16 hours, cooled, and 200 ml of saturated aqueous ammonium chloride are added. After 2 hours the organic layer is separated, dried and evaporated to yield the 2-(5-chloro-2-o-dimethylaminomethylphenyl)-oxazoline melting 70°–76°.

To the solution of 78 g thereof in 900 ml of methylene chloride, that of 29 g of cyanogen bromide in 290 ml of methylene chloride is added slowly while stirring at 0°. The mixture is stirred at room temperature for 16 hours and evaporated to yield the 6-(2-bromoethyl)-3-chloro-6,7-dihydrodibenz[c,e]azepin-5-one melting at 94°–97°.

The mixture of 34 g thereof, 1,100 ml of xylene and 12 g of potassium tert. butoxide is stirred and refluxed under nitrogen for 90 minutes. It is cooled, 5 g of activated charcoal are added, the mixture stirred 10 minutes, filtered and evaporated to yield the 3-chloro-6,7-dihydro-6-vinyl-dibenz[c,e]azepin-5-one melting at 170°–172°.

Analogously the 9-chloro-7-o-(methyl, methoxy, chloro and trifluoromethyl)-phenyl-5H-dibenz[c,e]azepine mesylates are prepared, melting at 230°–237°; 220°–226°; 229°–231° and 212°–214° respectively.

EXAMPLE 6

The solution of 3.2 g of 9-chloro-7-(o-fluorophenyl)-5H-dibenz[c,e]azepine and 2.0 g of m-chloroperbenzoic acid in 250 ml of methylene chloride is stirred for 16 hours at room temperature. It is washed with diluted aqueous sodium hydroxide, dried, evaporated and the residue crystallized from diethyl ether, to yield the 9-chloro-7-(o-fluorophenyl)-5H-dibenz[c,e]azepine-6-N-oxide melting at 166°–168°.

EXAMPLE 7

To the solution of 2.7 g of 2-[4-chloro-2-(2-fluorobenzoyl)-phenyl]-benzaldehyde in 10 ml of ethanol is added 30 ml of a saturated solution of ammonia in ethanol. The mixture is stirred at 25° for 4 days, evaporated and the residue dissolved in acetone. The solution is neutralized with ethereal hydrogen chloride to give 2.05 g of a crude mixture of two hydrochlorides. It is taken up in 50 ml of ethanol the solution heated on the steam bath for ¼ hour, filtered and the residue washed with cold ethanol, to yield the 5-amino-9-chloro-7-(o-fluorophenyl)-dibenz-[c,e]azepine melting at 255°–256°.

The combined mother liquors are chromatographed on silica gel plates using chloroform-ethyl acetate (4:1) as eluant, to give an additional amount (300 mg) of said 5-amine, as well as the 5-hydroxy-9-chloro-7-(o-fluorophenyl)-dibenz[c,e]azepine melting at 178°–181°.

The latter 5-alcohol can also be prepared by refluxing the mixture of 2.0 g of said starting aldehyde, 30 ml of isopropanol, 40 ml of concentrated aqueous ammonia, 3.85 g of ammonium acetate and 10 ml of water for a period of 4 days. After evaporation of the solvent the residue is partitioned between diethyl ether and aqueous sodium carbonate, the etheral layer is dried, evaporated and the residue crystallized from diethyl ether, to give 800 mg of said 5-alcohol, m.p. 180°–182°.

The starting material is prepared as follows: The solution of 3.2 g of 2-(o-bromomethylphenyl)-5-chloro-2'-fluorobenzophenone in 40 ml of freshly distilled dimethylsulfoxide is heated for 30 minutes in an oil bath at 178°. After cooling, the solution is partitioned between diethyl ether and water, the ethereal layer washed again with water and saturated aqueous sodium chloride, and evaporated. The residue is taken up in 40 ml of methylene chloride and the solution treated with 2.6 g of pyridinium chlorochromate for 2 hours at 25°. The mixture is diluted with 100 ml of diethyl ether, filtered through a bed of infusorial earth and the filtrate evaporated, to yield the 2-[4-chloro-2-(2-fluorobenzoyl)-phenyl]-benzaldehyde.

EXAMPLE 8

The mixture of 1.0 g of the 2-[4-chloro-2-(2-fluorobenzoyl)-phenyl]-benzaldehyde, 2.3 g of ammonium acetate and 30 ml of methanol is stirred at 25° for 16 hours and evaporated. The residue is taken up in methylene chloride, the solution washed with aqueous sodium bicarbonate, dried and evaporated. The foamy residue is taken up in hexane-diethyl ether (7:3), the solution filtered through a bed of silica gel, evaporated, and the residue crystallized from diethyl ether-hexane, to give the 5-methoxy-9-chloro-7-(o-fluorophenyl)-dibenz[c,e]azepine melting at 136°–138°.

EXAMPLE 9

Preparation of 10,000 tablets each containing 25 mg of the active ingredient:

| Formula: | |
|---|---|
| 9-chloro-7-(o-fluorophenyl)-5H-dibenz[c,e]azepine mesylate | 250.00 g |
| Lactose | 1,956.00 g |
| Corn Starch | 90.00 g |
| Polyethylene glycol 6,000 | 90.00 g |
| Talcum powder | 90.00 g |
| Magnesium stearate | 24.00 g |
| Purified water | q.s. |

Procedure

All the powders are passed through a screen with openings of 0.6 mm. Then the drug substance, lactose, talcum, magnesium stearate and half of the starch are mixed in a suitable mixer. The other half of the starch is suspended in 45 ml of water and the suspension added to the boiling solution of the polyethylene glycol in 180 ml of water. The paste formed is added to the powders which are granulated, if necessary, with an additional amount of water. The granulate is dried overnight at 35°, broken on a screen with 1.2 mm openings and compressed into tablets using concave punches with 7.1 mm diameter, uppers bisected.

Preparation of 10,000 capsules each containing 10 mg of the active ingredient:

| Formula: | |
|---|---|
| 9-chloro-7-(o-fluorophenyl)-5H-dibenz[c,e]azepine mesylate | 500.00 g |
| Lactose | 2,350.00 g |
| Corn starch | 150.00 g |

Procedure

All the powders are passed through a screen with openings of 0.6 mm. Then the drug substance is placed in a suitable mixer and mixed first with the talcum, then with the lactose until homogenous. No. 2 capsules are filled with 300 mg of the mixture, using a capsule filling machine.

Analogously tablets or capsules are prepares, containing any one of the compounds illustrated by the other examples herein.

What is claimed is:

1. A compound having the formula

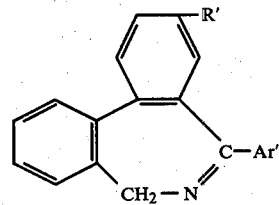

wherein Ar' is pyridyl and R' is fluoro, chloro, bromo or trifluoromethyl; or a pharmaceutically acceptable acid addition salt thereof.

2. A compound as claimed in claim 1, in which formula Ar' is 2-pyridyl and R' is bromo, fluoro or chloro; or a pharmaceutically acceptable acid addition salt thereof.

3. A compound as claimed in claim 1 and being the 9-chloro-7-(2-pyridyl)-5H-dibenz[c,e]azepine or a pharmaceutically acceptable acid addition salt thereof.

4. An anxiolytic, pharmaceutical composition comprising a correspondingly effective amount of a compound as claimed in claim 1, together with a pharmaceutical excipient.

5. A method of treating anxiety which comprises administering to said mammals enterally or parenterally an effective dosage of a composition as claimed in claim 4.

* * * * *